(12) United States Patent
Roehrig et al.

(10) Patent No.: US 7,889,896 B2
(45) Date of Patent: Feb. 15, 2011

(54) PATIENT WORKLIST MANAGEMENT IN DIGITAL RADIOGRAPHY REVIEW WORKSTATIONS

(75) Inventors: Jimmy R. Roehrig, Aptos, CA (US); Julian Marshall, Los Altos, CA (US)

(73) Assignee: Hologic, Inc., Marlborough, MA (US)

( * ) Notice: Subject to any disclaimer, the term of this patent is extended or adjusted under 35 U.S.C. 154(b) by 747 days.

(21) Appl. No.: 11/208,271

(22) Filed: Aug. 18, 2005

(65) Prior Publication Data

US 2007/0041623 A1 Feb. 22, 2007

(51) Int. Cl.
G06K 9/00 (2006.01)
(52) U.S. Cl. ............... 382/128; 382/100; 382/131; 382/284; 715/700; 715/763
(58) Field of Classification Search ......... 382/128, 382/305, 130, 131, 132; 600/407; 707/100; 345/634
See application file for complete search history.

(56) References Cited

U.S. PATENT DOCUMENTS

| | | | | |
|---|---|---|---|---|
| 5,815,591 | A * | 9/1998 | Roehrig et al. | 382/130 |
| 5,823,948 | A * | 10/1998 | Ross et al. | 600/300 |
| 5,917,929 | A * | 6/1999 | Marshall et al. | 382/128 |
| 6,067,373 | A * | 5/2000 | Ishida et al. | 382/130 |
| 6,873,717 | B2 * | 3/2005 | Lure et al. | 382/128 |
| 6,909,795 | B2 * | 6/2005 | Tecotzky et al. | 382/128 |
| 6,925,200 | B2 * | 8/2005 | Wood et al. | 382/132 |
| 6,970,587 | B1 * | 11/2005 | Rogers | 382/132 |
| 7,184,582 | B2 * | 2/2007 | Giger et al. | 382/128 |
| 7,187,790 | B2 * | 3/2007 | Sabol et al. | 382/128 |
| 7,383,237 | B2 * | 6/2008 | Zhang et al. | 706/20 |
| 7,383,307 | B2 * | 6/2008 | Kirkland et al. | 709/206 |
| 7,490,085 | B2 * | 2/2009 | Walker et al. | 707/10 |
| 2002/0186899 | A1 | 12/2002 | Bohnenkamp | |
| 2002/0193676 | A1 | 12/2002 | Bodicker et al. | |
| 2003/0013951 | A1 | 1/2003 | Stefanescu et al. | |
| 2003/0126148 | A1 * | 7/2003 | Gropper et al. | 707/100 |

(Continued)

FOREIGN PATENT DOCUMENTS

WO WO 2004/023790 A2 3/2004

OTHER PUBLICATIONS

Internet Access to Digital Medical X-rays by Image Features and Associated Text L. Rodney Long, George R. Thoma;National Library of Medicine, Bethesda, MD 20894; IEEE 1998.*

*Primary Examiner*—Wesley Tucker
*Assistant Examiner*—Nancy Bitar
(74) *Attorney, Agent, or Firm*—Brian J. Daiuto

(57) ABSTRACT

Managing a patient worklist in a radiology environment is described, the patient worklist identifying a plurality of medical imaging cases to be reviewed at a radiology review workstation. For each case, a set of CAD-computed metrics is received, the CAD-computed metrics being derived from an operation of a CAD processing algorithm on that case. According to a preferred embodiment, the cases in the patient worklist are sorted according to at least one of the CAD-computed metrics. The reviewing radiologist is provided with greater insight into, and control over, patient workflow at the radiology review workstation. Also described is a graphical user interface for easy user customization of the case sorting criteria. Examples of case sorting criteria include a number of CAD markers per case metric, a maximum suspiciousness metric, and an anatomical complexity metric.

19 Claims, 5 Drawing Sheets

U.S. PATENT DOCUMENTS

| | | | |
|---|---|---|---|
| 2005/0096530 A1* | 5/2005 | Daw et al. | 600/408 |
| 2006/0000884 A1* | 1/2006 | Menhardt et al. | 235/375 |
| 2006/0215894 A1* | 9/2006 | Lakare | 382/128 |
| 2007/0003119 A1* | 1/2007 | Roehrig et al. | 382/128 |
| 2007/0041623 A1* | 2/2007 | Roehrig et al. | 382/128 |
| 2007/0083849 A1* | 4/2007 | Stoval, III | 717/104 |
| 2007/0280530 A1* | 12/2007 | Fung et al. | 382/159 |
| 2008/0095418 A1* | 4/2008 | Moriya | 382/128 |
| 2008/0125643 A1* | 5/2008 | Huisman et al. | 600/420 |

* cited by examiner

| # CAD MARKERS | PATIENT NAME | ACQUISITION DATE/TIME | MAX SUSP. | BREAST DENSITY | (OTHER CAD-COMPUTED METRICS...) |
|---|---|---|---|---|---|
| 5 | SMITH, M. | 2005-03-21 13:27 | 0.6 | 0.4 | : |
| 4 | JONES, N. | 2005-03-21 08:22 | 0.9 | 0.3 | : |
| 4 | WILLIAMS, O. | 2005-03-21 14:55 | 0.7 | 0.5 | : |
| 4 | CAMPBELL, A. | 2005-03-21 18:02 | 0.8 | 0.1 | : |
| 2 | KLEIN, M. | 2005-03-21 16:19 | 0.8 | 0.3 | : |
| 2 | WANG, L. | 2005-03-21 17:11 | 0.6 | 0.9 | |
| 2 | GARCIA, M. | 2005-03-21 18:24 | 0.6 | 0.9 | |
| ... | ... | ... | ... | ... | ... |

FIG. 4

PATIENT WORKLIST MANAGEMENT IN DIGITAL RADIOGRAPHY REVIEW WORKSTATIONS

FIELD

This patent specification relates to medical imaging. More particularly, this patent specification relates to management of patient worklists in digital radiography review workstations.

BACKGROUND

An ongoing tension is found in today's radiology environment between providing high-quality image review and maintaining adequate patient throughput to keep costs under control. Despite ongoing advances in imaging technology and related data processing systems, it is the radiologist who continues to bear the burden of the cost-quality tradeoff. As used herein, radiologist generically refers to a medical professional that analyzes medical images and makes clinical determinations therefrom, it being understood that such person might be titled differently, or might have differing qualifications, depending on the country or locality of their particular medical environment.

With the best of intentions, the medical imaging equipment industry continues to develop more technology to provide more image information and/or more decision support information to the radiologist for detecting and/or diagnosing a particular condition. However, especially in high-throughput environments such as x-ray mammography breast cancer screening environments, this additional information can sometimes frustrate the radiologist, already pressured by workload and cost considerations, by adding another layer of complexity to the process, and/or by presenting the additional information in awkward or non-intuitive user interfaces.

Even subtle user interface issues associated with image presentation tools and/or decision support tools can have a significant impact on the radiologist review rate and/or the quality of detection/diagnosis. One such user interface issue relates to patient worklists (i.e., case worklists) identifying the medical imaging cases to be presented to the radiologist at a radiography review workstation. Although some proposals have been made in relation to customization of patient worklists, such as those discussed in U.S. 2003/0126148 A1, which is incorporated by reference herein, it is believed that further improvements are needed. Other issues arise as would be apparent to one skilled in the art upon reading the present disclosure. It would be desirable to provide for enhanced radiologist insight into, and control over, patient worklists at a radiology review workstation.

SUMMARY

A system, method, and associated computer program products are provided for facilitating management of a patient worklist in a radiology environment, the patient worklist identifying a plurality of medical imaging cases to be reviewed at a radiology review workstation. For each case, a set of CAD-computed metrics is received, the CAD-computed metrics being derived from an application of a CAD processing algorithm to that case. According to a preferred embodiment, the cases in the patient worklist are sorted according to at least one of the CAD-computed metrics. The reviewing radiologist is provided with greater insight into, and control over, patient workflow at the radiology review workstation.

Also provided is a graphical user interface for easy user customization of case sorting criteria. Examples of case sorting criteria include, but are not limited to: a number of CAD markers per case metric; a maximum suspiciousness metric; and an anatomical complexity metric. The sorting criteria can optionally include other case-related metrics such as clinical metrics (e.g., weight, family history) and demographic metrics (e.g., race, HMO type, etc.).

BRIEF DESCRIPTION OF THE DRAWINGS

FIG. 4 illustrates a patient worklist display according to a preferred embodiment.

DETAILED DESCRIPTION

Figure 1:
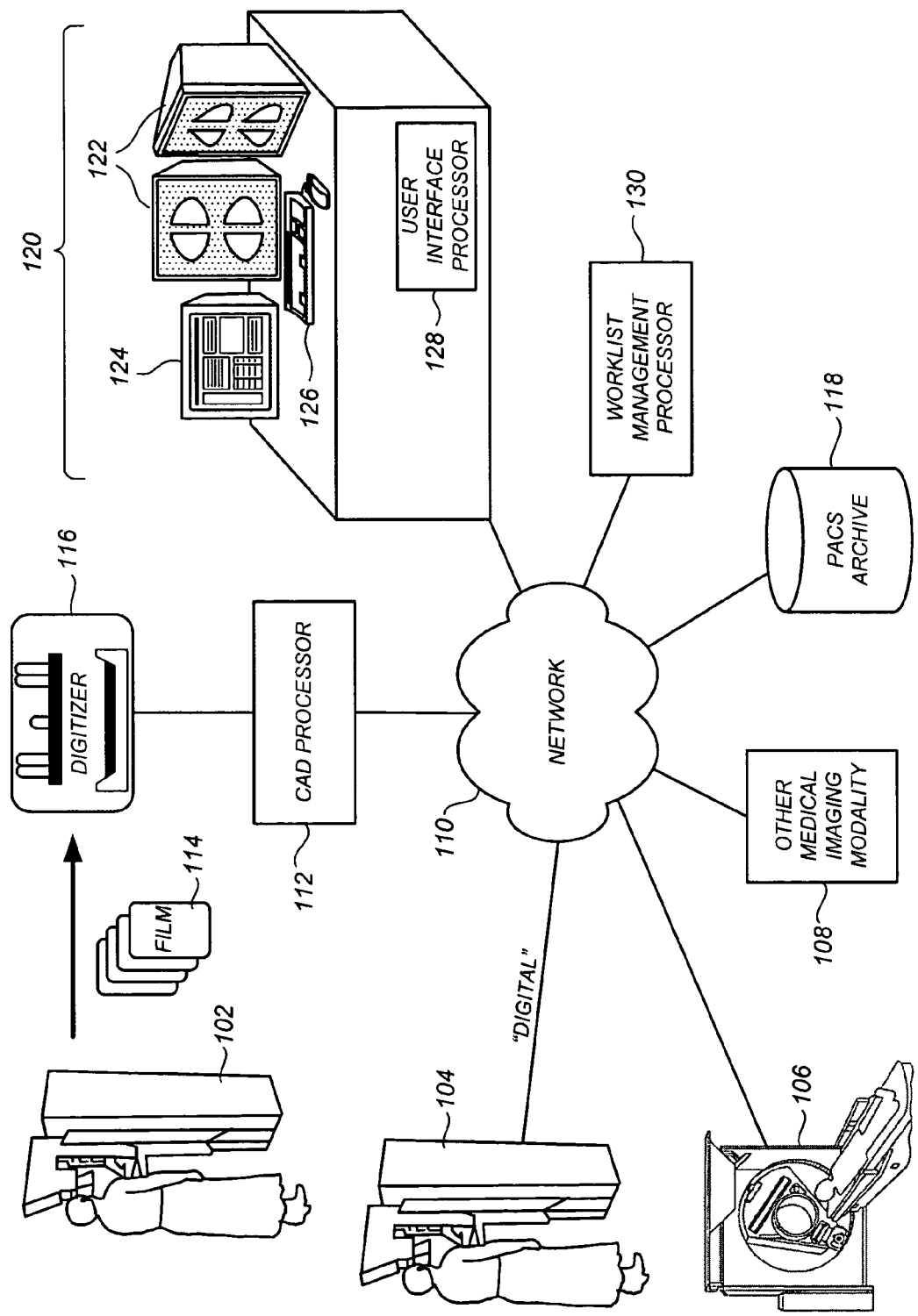
FIG. 1 illustrates a conceptual diagram of a medical imaging environment including a review workstation according to a preferred embodiment.

FIG. 1 illustrates a conceptual diagram of a medical imaging environment for which one or more of the preferred embodiments is particularly suited. Shown in FIG. 1 is a network 110, which may be a HIS/RIS (Hospital Information System/Radiology Information System) network, to which is coupled a film mammogram acquisition device 102, a digital mammogram acquisition device 104, a computed tomography (CT) acquisition device 106, and a generalized "other" medical imaging device 108. A computer-aided detection (CAD) processor 112 coupled to the network 110 receives digital medical images from one or more of the devices 104-108, and/or from a digitizer 116 that digitizes x-ray mammogram films 114 generated by the film mammogram acquisition device 102. The CAD processor 112 processes the medical images according to a CAD processing algorithm. The medical images are then viewed in conjunction with the associated CAD results at a radiology review workstation 120.

Preferably, the various medical images and related information are communicated according to the DICOM (Digital Imaging and Communications in Medicine) standard and the network 110 supports the TCP/IP protocol, which is used as the transport protocol for the DICOM standard. Also coupled to the network 110 is a PACS (Picture Archiving and Communication System) archive 118, generally representing a repository for medical information associated with the medical imaging environment, including both current and archived images, current and archived CAD results, radiology reports for completed cases, and so forth.

Computer-aided detection (CAD) generally refers to the use of computers to analyze medical images to detect anatomical abnormalities therein. Sometimes used interchangeably with the term computer-aided detection are the terms computer-aided diagnosis, computer-assisted diagnosis, or computer-assisted detection. As used herein, CAD detection refers to a location in a medical image that a CAD system, in accordance with a CAD processing algorithm operating on the medical image, has identified as warranting some type of attention by a radiologist.

As known in the art, a CAD algorithm usually identifies a preliminary set of candidate detections in a medical image and then selects which ones, if any, will qualify as actual CAD detections based on a variety of computed features associated with the candidate detections. The CAD results, i.e., the body of information associated with the operation of the CAD algorithm on the medical image, are most often communicated in the form of annotation maps comprising graphical annotations (CAD markers) overlaid on a diagnostic-quality or reduced-resolution version of the medical image, one CAD marker for each CAD detection. CAD results are mainly used by radiologists as "secondary reads" or secondary diagnosis tools. When analyzing a medical image, the radiologist usually makes his or her own analytical determinations before looking at the CAD results, which either verify those determinations or trigger further inspection of the image. Some CAD implementations have used CAD results in a "concurrent reading" context in which the radiologists look at the CAD results at the same time that they look at the images.

In the field of x-ray mammography, thousands of mammography CAD systems are now installed worldwide, and are used to assist radiologists in the interpretation of millions of mammograms per year. Mammography CAD systems are described, for example, in U.S. Pat. Nos. 5,729,620, 5,815,591, 5,917,929, 6,075,879, 6,266,435, 6,434,262, and U.S. Pat. No. 6,901,156, each of which is incorporated by reference herein. Mammography CAD algorithms analyze digital or digitized images of standard mammographic views (e.g. CC, MLO) for characteristics commonly associated with breast cancer, such as calcifications, masses, and architectural distortions.

As indicated by the presence of the CT acquisition device 106 and the "other" medical imaging device 108 in FIG. 1, the preferred embodiments described herein are readily applicable for a variety of present or prospective non-mammography medical imaging modalities such as CT, MRI, PET, SPECT, ultrasound, x-ray tomosynthesis, thermography, electrical conductivity-based modalities, and other modalities. In the field of chest CT imaging, at least one CAD system has been commercialized for assisting radiologists in the detection of suspicious lung nodules, such systems being referenced herein as lung-CT CAD systems. Examples of lung-CT CAD systems are described in U.S. Pat. No. 5,881,124 and in the commonly assigned U.S. Pat. No. 6,925,200, each of which is incorporated by reference herein.

The preferred embodiments described herein are seamlessly layered upon an existing CAD workflow, in which the digital or digitized medical images are processed by the CAD processor 112, and in which the medical images and their related CAD results are subsequently displayed at the review workstation 120 to a viewer, who makes a clinical determination therefrom. The clinical determination can be in relation to screening, diagnosis, follow-up, or any of a variety of other activities. Notably, the preferred embodiments herein are particularly advantageous in a screening context for which speed, case throughput, and viewer stamina are important factors.

In one preferred embodiment, the review workstation 120 comprises a multi-modality workstation adapted and configured for a mammography environment. In one example, a Sectra IDS5/mx.net dedicated mammography workstation can be used that allows for third-party plug-ins, including plug-ins providing the CAD user interfacing functionalities described herein. Review workstation 120 comprises a diagnostic display 122, an administrative display 124, user input devices 126 (e.g., keyboard, mouse, trackball, pointers, etc), and a user interface processor 128. Administrative display 124 is used for input and output of a wide variety of information that may be associated with a particular set of medical images (e.g., listings, tables, plots, text descriptions, etc), as well as for system installation, maintenance, updating, and related tasks.

Also illustrated in FIG. 1 is a worklist management processor 130 configured and adapted to implement the patient worklist processing functionalities described herein. It is to be appreciated, however, that such patient worklist processing can be performed by any combination of the user interface processor 128, the CAD processor 112, and the worklist management processor 130, or by any other processor or combination of processors (such as HIS/RIS scheduling processors) coupled to the network 110, without departing from the scope of the preferred embodiments.

Notably, the medical imaging environment of FIG. 1 is presented by way of example only and is not intended to limit the scope of the preferred embodiments to this particular scenario. By way of example, different combinations of the devices of FIG. 1 can be placed adjacently to each other or integrated into the same hardware boxes without departing from the scope of the preferred embodiments. By way of still further example, the network 110 can be a wide-area network with the different nodes being distributed throughout a city, a country, or the world. Alternatively, and by way of still further example, some or all of the transfer of digital information can be achieved by physical transfer of disks, memory sticks, or other digital media devices without departing from the scope of the preferred embodiments. In view of the present disclosure, a person skilled in the art would be able to construct such plug-ins or other software packages capable of achieving the described user interfaces and processing functionalities without undue experimentation, using publicly available programming tools and software development platforms.

Figure 2A:
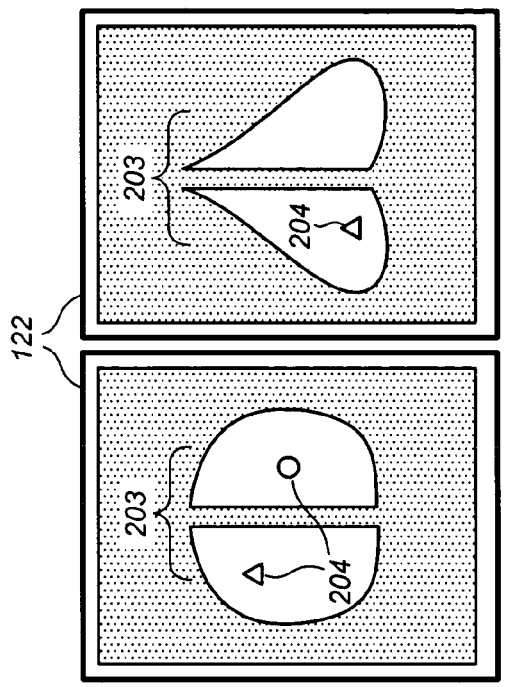
FIGS. 2A and 2B illustrate review workstations according to preferred embodiments displaying mammogram image information and lung-CT image information, respectively.
Figure 2A:
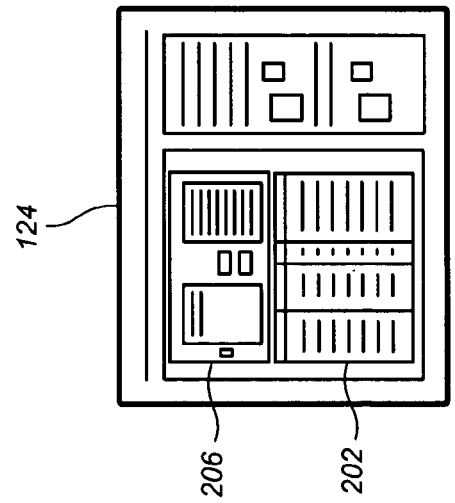
Figure 2B:
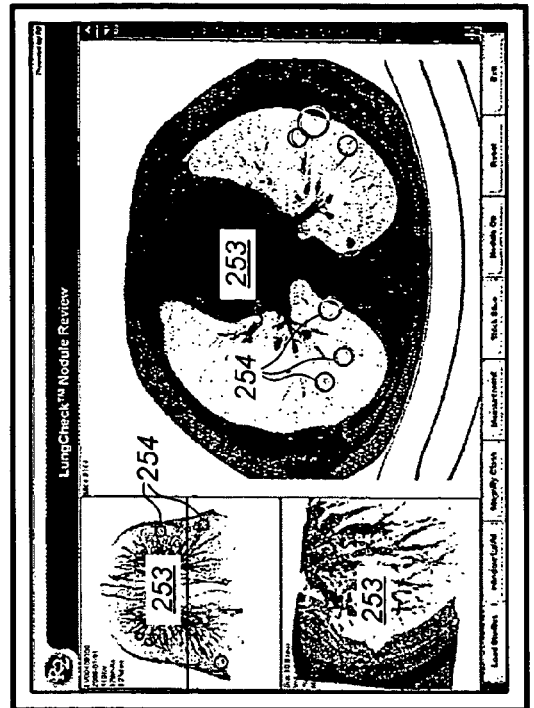
Figure 2B:
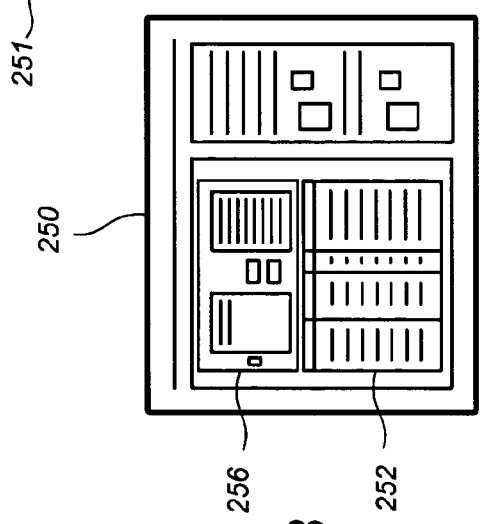

FIGS. 2A and 2B illustrate radiology review workstations according to a preferred embodiment displaying mammogram image information and CT-lung image information, respectively. In FIG. 2A, the diagnostic display 122 presents mammogram images 203 annotated according to mammography CAD detections 204. In FIG. 2B, a diagnostic display 251 presents lung-CT images 253 annotated according to lung-CT CAD detections 254. In FIG. 2A, the administrative display 124 includes a patient worklist display 202, as well as a patient worklist priority rule modification display 206. In FIG. 2B, an administrative display 250 includes a patient worklist display 252, as well as a patient worklist priority rule modification display 256. With respect to basic structure and interfacing functionality as described further herein, the patient worklist displays 202 and 252 are similar to each other and the patient worklist priority rule modification displays 206 and 256 are similar to each other, although many of the CAD-computed metrics, clinical metrics, and/or demographic metrics may differ.

Figure 3:
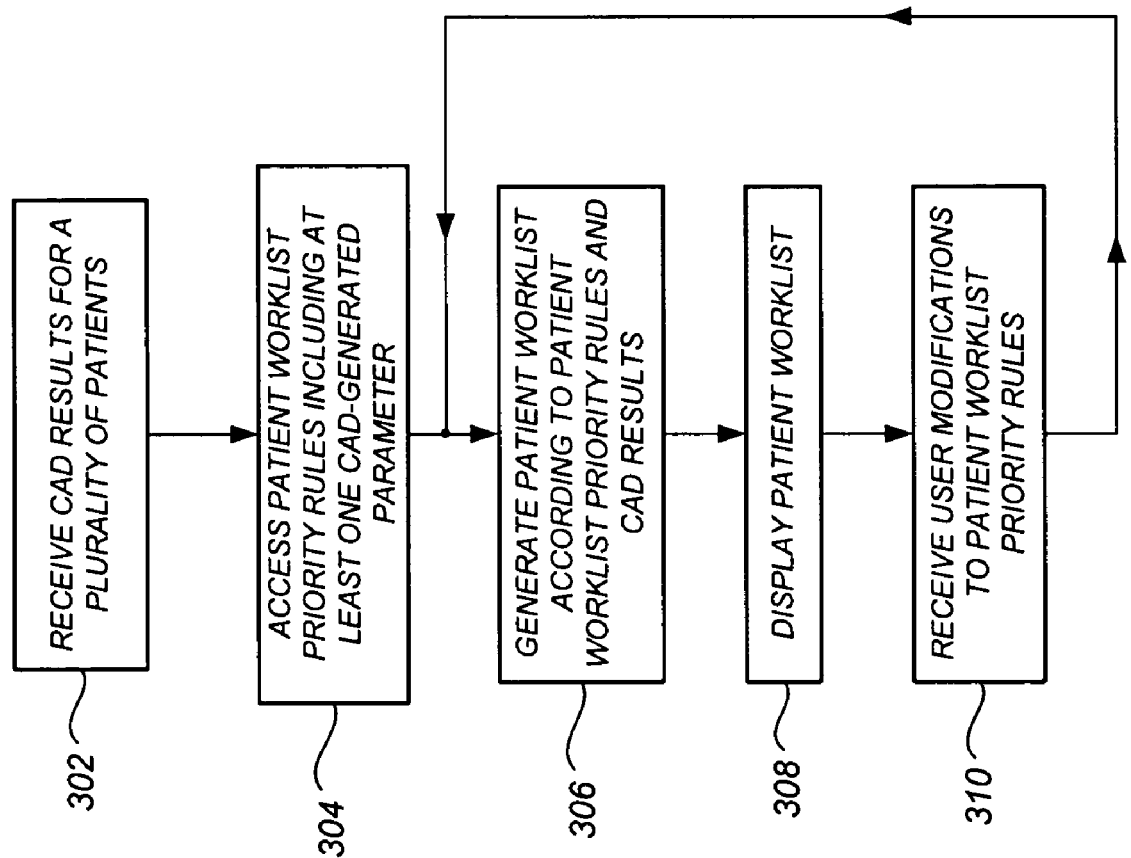
FIG. 3 illustrates patient worklist management according to a preferred embodiment.

FIG. 3 illustrates patient worklist management according to a preferred embodiment. At step 302, CAD results for a plurality of medical imaging cases are received. At step 304, patient worklist priority rules are accessed, the patient worklist priority rules defining a sorting hierarchy including at least one CAD-computed metric. The patient worklist priority rules may comprise a default set when no customizations have been received, or may comprise a customized set when customizations have been received. For one preferred embodiment, CAD-computed metric refers to (i) features computed by a CAD processing algorithm while operating on a medical imaging case to detect anatomical abnormalities therein, as well as (ii) various logical or mathematical formulations based on such features. For other preferred embodiments, CAD-computed metric can further refer to one or more features extracted from a medical imaging case for the particular purpose of providing a basis for worklist prioritization. At step 306, the patient worklist is sorted according to the patient worklist priority rules and CAD-computed metrics. At step 308, the patient worklist is displayed to the radiologist. At step 310, modifications to the patient worklist priority rules are received from the radiologist, preferably using a graphical user interface as described hereinbelow, followed again by the sorting and display steps 306 and 308. For newly received medical imaging cases and their associated CAD results, entries are dynamically entered into the patient worklist according to the current sorting hierarchy.

FIG. 4 illustrates a patient worklist display 402 according to a preferred embodiment for a mammography review workstation, showing the results of but one of a wide variety of different sorting hierarchies that are within the scope of the present teachings. Patient worklist display 402 comprises an ordered listing of cases sorted by a number of CAD markers field 406 as a primary sort key, descending, and by a case acquisition date/time field 410 as a secondary sort key, ascending, such that older cases have priority over newer cases for a common number of CAD markers. Also displayed, by way of nonlimiting example, is a patient name field 408, a maximum suspiciousness field 412, and a breast density field 414.

Column heading buttons 404 are provided as shown in FIG. 4. In one preferred embodiment, the user may dynamically change the patient worklist priority rules by pressing one of the column heading buttons 404, the most recently-pressed button representing the primary sort key, the previously-pressed button representing the secondary sort key, and so on. The directional order for the primary sort key can be toggled between ascending and descending by serially pressing the column heading button 404 associated with the current primary sort key. Any of a variety of differing graphical user interface schemes for achieving similar customization functions as shown in FIG. 4 are within the scope of the preferred embodiments.

Figure 5:
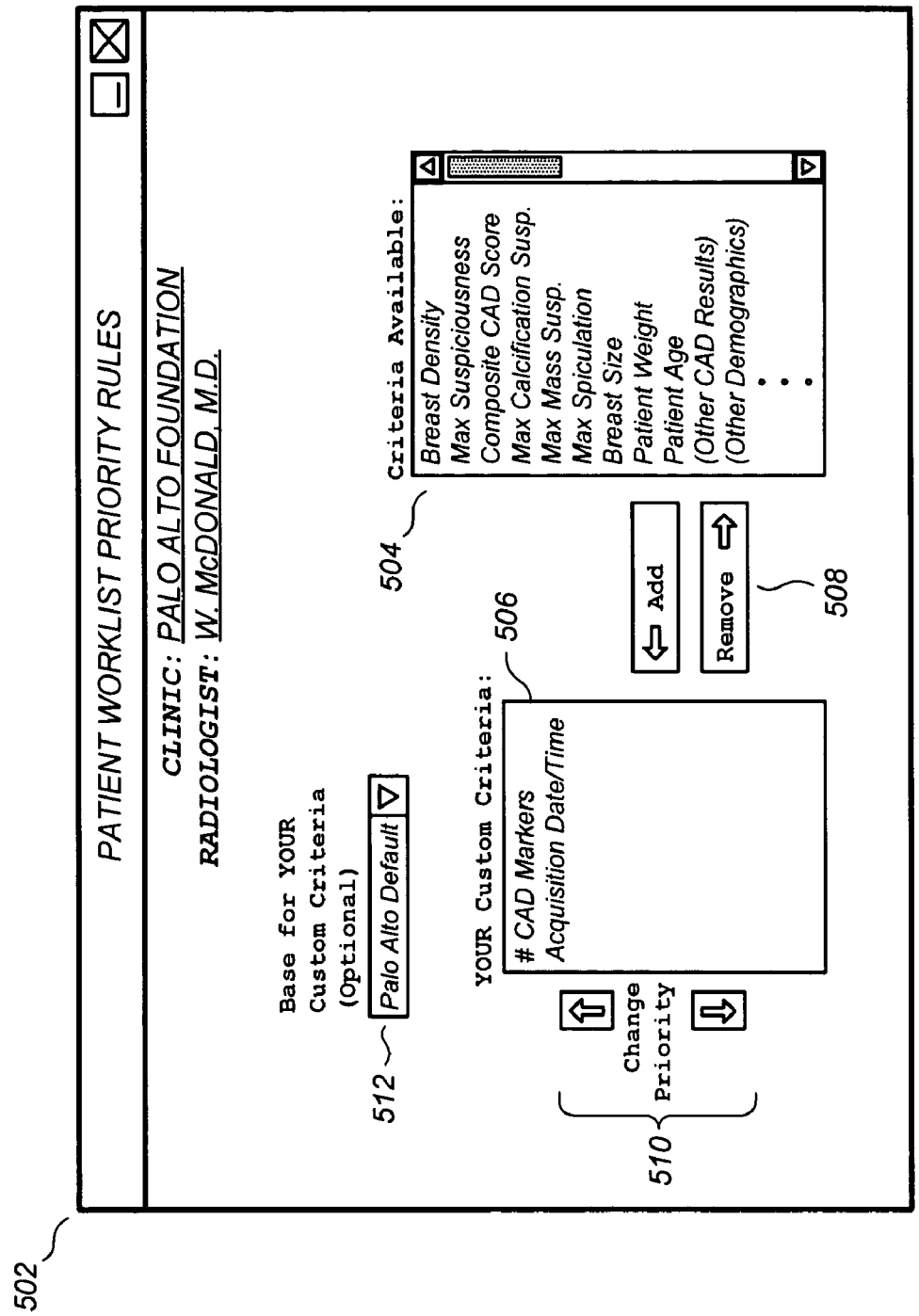
FIG. 5 illustrates a patient worklist priority rule modification display according to a preferred embodiment.

FIG. 5 illustrates a patient worklist priority rule modification display 502 according to a preferred embodiment for a mammography review workstation, which is preferably overlayable on the administrative display 206/256 in a Windows®-like fashion. A predetermined list of sorting criteria 504 is provided including at least one CAD-computed metric. In one preferred embodiment (not shown), the sorting criteria 504 are strictly limited to CAD-computed metrics such as, but not limited to: a total number of CAD markers metric, a breast density metric, a breast size metric, a maximum overall suspiciousness metric, a maximum calcification suspiciousness metric, and a maximum mass suspiciousness metric. In another preferred embodiment, the sorting criteria 504 can include other case-related metrics such as clinical metrics (e.g., weight, family history) and/or demographic metrics (e.g., race, HMO type, etc.). While differing CAD algorithms will often have different nomenclatures and scalings, there can often be an "ultimate" or "overall" scalar score assigned to a case, termed herein a composite CAD score, which can be based on the medical image data in optional combination with clinical data and/or demographic data. In another preferred embodiment, the sorting criteria 504 further includes the composite CAD score.

Patient worklist priority rule modification display 502 further comprises a priority rule display 506 listing the currently-selected sorting hierarchy. Sorting criteria can be added and removed by add/remove buttons 508, with the priority (i.e., primary sort key, secondary sort key, tertiary sort key) being changeable using priority change buttons 510. Optionally, the user can start by choosing from a variety of pre-programmed priority rules (e.g., clinic default priority rules, saved customization choices made by other radiologists or radiologist groups, etc.) using the pull-down menu 512.

The patient worklist display 402 of FIG. 4 and the patient worklist priority rule modification display 502 of FIG. 5 are readily applicable for any imaging modality by changing the available fields and sorting criteria 504 as needed. For example, in a lung-CT environment, the CAD-computed metrics in sorting criteria 504 may comprise a number of detected lung nodules per case metric and a lung nodule size metric. One particularly useful sorting criteria usually applicable for most modalities is an anatomical complexity metric (e.g., breast density for mammography, lung complexity for lung-CT, colon length for virtual colonoscopy, etc.), with radiologist review effort usually increasing for cases of increased anatomical complexity.

Thus, in accordance with one or more advantages according to the preferred embodiments, the radiologist is provided with increased insight into their patient workflow and increased control over their patient workflow. In turn, this can increase radiologist efficiency, stamina, and even attitude toward that day's workload. By way of example, a first radiologist who is a self-considered "morning person" may elect to sort the patient worklist by decreasing breast density so that they will review these more difficult cases while fresh and alert in the morning. A second radiologist who is an "evening person" may do the opposite (i.e., sort by increasing breast density). More generally, a rich variety of custom worklist prioritization scenarios is provided that can allow each user (or group of users) to best match the patient review sequence to their personal habits, mental or physical biorhythms, experience levels, etc.

An additional advantage of worklist management according to one or more of the preferred embodiments is that there is very little added complexity, from both a HIS/RIS/PACS perspective and from an end user perspective. This is because, preferably, the same CAD processing algorithm is used for both abnormality detection and for worklist management. Accordingly, very little additional CAD processing hardware or CAD processing time is needed, because most of the CAD-computed features useful for worklist prioritization are already computed as part of the abnormality detection computations. Likewise, the amount of additional training needed by the radiologist to understand and manage the worklists is generally small, because they are already familiar with the CAD-computed worklist prioritization features from their normal training in CAD-assisted case viewing.

Whereas many alterations and modifications of the present invention will no doubt become apparent to a person of ordinary skill in the art after having read the foregoing description, it is to be understood that the particular embodiments shown and described by way of illustration are in no way intended to be considered limiting. By way of example, the described CAD-based patient worklist prioritization is readily applied in a centralized radiology workload planning context without departing from the scope of the preferred embodiments. For example, according to another preferred embodiment, an aggregate patient worklist for an entire clinic is sorted according to one or more CAD-generated parameters for overview by a head radiologist, hospital administrator etc. As another example, case routing may be implemented based on the generated patient worklist, e.g., with mostly-dense breasts being routed to a first radiologist (or first group of radiologists) for review, and with mostly-fatty breasts being routed to a second radiologist (or second group of radiologists) for review. Such case routing may be particularly advantageous in a radiologist training context, where cases can be routed based on trainee status. More complex routing scenarios (in which expert systems might be used, for example) based on static or dynamic routing models having one or more CAD-generated routing criteria are also within the scope of the preferred embodiments.

By way of further example, the described CAD-based patient worklist prioritization is readily applied in a distributed or tele-PACS environment, each remote radiologist being provided with advantageous insight into and/or control over their patient worklist. Judicious case routing based on the CAD-generated parameters can also be implemented in this context, e.g., by routing cases with high maximum suspiciousness to a local group of radiologists, and by sending other cases to overseas radiologists.

By way of even further example, it is to be appreciated that the sorting order for a particular criterion may be something other than monotonically-increasing or monotonically-decreasing—for example, "structured" or even "purposefully random"—without departing from the scope of the preferred embodiments. By way of example, a particular radiologist might wish for their workload to purposefully alternate between marked cases (i.e., cases having one or more CAD markers) and unmarked cases, to keep their attention fresh or otherwise temporally balanced. Therefore, reference to the details of the preferred embodiments are not intended to limit their scope, which is limited only by the scope of the claims set forth below.

What is claimed is:

1. A method for presenting a plurality of medical imaging cases to a radiologist at a radiology review workstation, comprising:
    receiving for each of said plurality of medical imaging cases a set of CAD-computed metrics derived from an operation of a CAD processing algorithm thereon, said CAD processing algorithm detecting anatomical abnormalities in each of said plurality of medical imaging cases for presentation therewith at the radiology review workstation;
    receiving at least one input from the radiologist identifying at least one CAD-computed metric according to which a patient worklist identifying the plurality of medical imaging cases is to be sorted, wherein said identified at least one CAD-computed metric comprises at least one image-based feature as computed by said CAD processing algorithm for each of said plurality of medical imaging cases;
    sorting the patient worklist according to said identified at least one CAD-computed metric; and
    sequentially displaying to the radiologist the plurality of medical imaging cases according to their order of appearance in the sorted patient worklist;
    wherein said identified at least one CAD-computed metric includes an anatomical complexity metric, whereby said sorting the patient worklist comprises sorting the patient worklist according to said anatomical complexity metric.

2. The method of claim 1, further comprising displaying the sorted patient worklist to the radiologist at the radiology review workstation.

3. The method of claim 2, said sorting being in accordance with a sorting hierarchy customized by the radiologist using a graphical user interface.

4. The method of claim 3, said customizing comprising selecting a desired sorting criterion by clicking on a column heading of a currently displayed patient worklist.

5. The method of claim 3, said customizing comprising selecting desired sorting criteria from a predetermined list of sorting criteria provided on said graphical user interface, said predetermined list including said at least one CAD-computed metric.

6. The method of claim 5, said predetermined list further including at least one clinical sorting criterion and at least one demographic sorting criterion.

7. The method of claim 1, wherein said patient worklist is sorted according to a total number of CAD markers per case.

8. The method of claim 1, said radiology review workstation being a mammography review workstation, wherein said patient worklist is sorted according to a sorting criterion selected from the group consisting of: a total number of CAD markers metric, a breast density metric, a breast size metric, a maximum overall suspiciousness metric, a maximum calcification suspiciousness metric, and a maximum mass suspiciousness metric.

9. The method of claim 1, said radiology review workstation being a CT-lung review workstation, wherein said patient worklist is sorted according to a sorting criterion selected from the group consisting of: a number of detected lung nodules per case metric, and a lung nodule size metric.

10. A radiology review workstation, comprising:
    a medical image display sequentially displaying to a radiologist a plurality of medical imaging cases annotated with CAD markers identifying anatomical abnormalities therein detected by CAD processing thereof; and
    a patient worklist user interface (i) receiving for each of said plurality of medical imaging cases a set of CAD-computed metrics derived from said CAD processing thereof, (ii) receiving at least one input from the radiologist identifying at least one CAD-computed metric according to which a case worklist identifying the medical imaging cases to be displayed on said medical image display is to be sorted, and (iii) sorting the case worklist according to the identified at least one CAD-computed metric;
    wherein said at least one CAD-computed metric according to which the case worklist is sorted comprises at least one image-based feature as computed by said CAD processing of each of said plurality of cases;
    wherein the medical image display sequentially displays the plurality of medical imaging cases according to an order of the sorted case worklist;
    and wherein said identified at least one CAD-computed metric includes an anatomical complexity metric, whereby said patient worklist is sorted according to said anatomical complexity metric.

11. The radiology review workstation of claim 10, the patient worklist user interface displaying a list of predetermined sorting criteria including said at least one CAD-computed metric, said radiologist input identifying the at least one CAD-computed metric from the displayed list.

12. The radiology review workstation of claim 11, said list of predetermined sorting criteria further including at least one clinical sorting criterion and at least one demographic sorting criterion.

13. The radiology review workstation of claim 10, wherein said case worklist is sorted according to one of a total number of CAD markers per case and said anatomical complexity metric.

14. The radiology review workstation of claim 10, said radiology review workstation being a mammography review workstation, wherein said case worklist is sorted according to a sorting criterion selected from the group consisting of: a total number of CAD markers metric, a breast density metric, a breast size metric, a maximum overall suspiciousness metric, a maximum calcification suspiciousness metric, and a maximum mass suspiciousness metric.

15. A computer program product embodied on a non-transitory computer readable medium for presenting a plurality of medical imaging cases to a radiologist at a radiology review workstation, comprising:
   computer code for receiving, for each of said plurality of medical imaging cases, a set of CAD-computed metrics derived from an operation of a CAD processing algorithm thereon, said CAD processing algorithm detecting anatomical abnormalities in each of said plurality of medical imaging cases for presentation therewith at the radiology review workstation;
   computer code for receiving at least one input from the radiologist identifying at least one CAD-computed metric according to which a patient worklist identifying the plurality of medical imaging cases is to be sorted, wherein said identified at least one CAD-computed metric comprises at least one image-based feature as computed by said CAD processing algorithm for each of said plurality of medical imaging cases;
   computer code for sorting the patient worklist according to said identified at least one CAD-computed metric; and
   computer code for sequentially displaying to the radiologist the plurality of medical imaging cases according to their order of appearance in the sorted patient worklist;
   wherein said identified at least one CAD-computed metric includes an anatomical complexity metric, whereby said computer code for sorting the patient worklist comprises computer code for sorting the patient worklist according to said anatomical complexity metric.

16. The computer program product of claim 15, further comprising computer code for displaying the sorted patient worklist to the radiologist at the radiology review workstation.

17. The computer program product of claim 16, further comprising computer code for displaying a list of predetermined sorting criteria including said at least one CAD-computed metric, said radiologist input identifying the at least one CAD-computed metric from the displayed list.

18. The computer program product of claim 17, said list of predetermined sorting criteria further including at least one clinical sorting criterion and at least one demographic sorting criterion.

19. The computer program product of claim 15, wherein said patient worklist is sorted according to one of a total number of CAD markers per case and said anatomical complexity metric.

* * * * *